United States Patent
Xia et al.

(10) Patent No.: US 10,239,969 B2
(45) Date of Patent: *Mar. 26, 2019

(54) SPHERICAL MAGNESIUM HALIDE ADDUCT, A CATALYST COMPONENT AND A CATALYST FOR OLEFIN POLYMERIZATION PREPARED THEREFROM

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Xianzhi Xia, Beijing (CN); Yuexiang Liu, Beijing (CN); Jigui Zhang, Beijing (CN); Xinsheng Wang, Beijing (CN); Ping Gao, Beijing (CN); Suzhen Qiao, Beijing (CN); Maoping Yin, Beijing (CN); Weili Li, Beijing (CN); Tianyi Zhang, Beijing (CN); Renqi Peng, Beijing (CN); Ying Chen, Beijing (CN); Zhihui Zhang, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 9 days.

This patent is subject to a terminal disclaimer.

(21) Appl. No.: 15/292,467

(22) Filed: Oct. 13, 2016

(65) Prior Publication Data
US 2017/0101486 A1    Apr. 13, 2017

Related U.S. Application Data

(62) Division of application No. 13/384,419, filed as application No. PCT/CN2009/000796 on Jul. 15, 2009, now Pat. No. 9,499,569.

(51) Int. Cl.
*C07F 3/00* (2006.01)
*C08F 110/06* (2006.01)
*C08F 10/00* (2006.01)

(52) U.S. Cl.
CPC ............ *C08F 110/06* (2013.01); *C07F 3/003* (2013.01); *C08F 10/00* (2013.01)

(58) Field of Classification Search
None
See application file for complete search history.

(56) References Cited

U.S. PATENT DOCUMENTS

| 4,069,169 A | 1/1978 | Toyoda et al. |
| 4,276,193 A | 6/1981 | Arlt et al. |
| 4,301,029 A | 11/1981 | Caunt et al. |
| 4,399,054 A | 8/1983 | Ferraris et al. |
| 4,421,674 A | 12/1983 | Invernizzi et al. |
| 4,469,648 A | 9/1984 | Ferraris et al. |

(Continued)

FOREIGN PATENT DOCUMENTS

| CN | 85101441 | 1/1987 |
| CN | 1020448 | 5/1993 |

(Continued)

OTHER PUBLICATIONS

Machine Translation of CN 1743347 A, ProQuest Dialog, 2014.
Office Action dated Nov. 29, 2013, issued in Malaysian Application No. PI 2012000047.
PCT International Search Report dated Apr. 22, 2010, for International Application No. PCT/CN2009/000796.
PCT International Preliminary Report on Patentability dated Jan. 17, 2012, for International Application No. PCT/CN2009/000796.

(Continued)

*Primary Examiner* — Nicole M. Buie-Hatcher
(74) *Attorney, Agent, or Firm* — Finnegan, Henderson, Farabow, Garrett & Dunner LLP

(57) ABSTRACT

A magnesium halide adduct represented by the formula (I): $MgX_2 \cdot mROH \cdot nE \cdot pH_2O$, in which X is chlorine, bromine, a $C_1$-$C_{12}$ alkoxy, a $C_3$-$C_{10}$ cycloalkoxy or a $C_6$-$C_{10}$ aryloxy, with the proviso that at least one X is chlorine or bromine; R is a $C_1$-$C_{12}$ alkyl, a $C_3$-$C_{10}$ cycloalkyl or a $C_6$-$C_{10}$ aryl; E is an o-alkoxybenzoate compound represented by the formula (II): in which $R_1$ and $R_2$ groups are independently a $C_1$-$C_{12}$ linear or branched alkyl, a $C_3$-$C_{10}$ cycloalkyl, a $C_6$-$C_{10}$ aryl, a $C_7$-$C_{10}$ alkaryl or an $C_7$-$C_{10}$ aralkyl, the $R_1$ and $R_2$ groups are identical to or different from the R group; m is in a range of from 1.0 to 5.0; n is in a range of from 0.001 to 0.5; and p is in a range of from 0 to 0.8, is disclosed. A catalyst component useful in olefin polymerization, which comprises a reaction product of (1) the magnesium halide adduct, (2) a titanium compound, and optionally (3) an electron donor compound, is also disclosed.

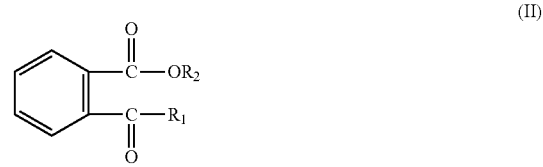

(II)

13 Claims, No Drawings

(56) References Cited

U.S. PATENT DOCUMENTS

| | | | |
|---|---|---|---|
| 4,563,512 A | 1/1986 | Goodall | |
| 5,095,153 A | 3/1992 | Agnes et al. | |
| 5,100,849 A | 3/1992 | Miya et al. | |
| 5,476,824 A | 12/1995 | Koskinen et al. | |
| 6,020,279 A | 2/2000 | Uwai et al. | |
| 6,127,304 A | 10/2000 | Sacchetti et al. | |
| 6,323,152 B1 | 11/2001 | Sacchetti et al. | |
| 7,049,377 B1 | 5/2006 | Morini et al. | |
| 7,332,455 B2 | 2/2008 | Wei et al. | |
| 9,353,197 B2 * | 5/2016 | Xia | C08F 10/00 |
| 2005/0096389 A1 | 5/2005 | Gao et al. | |
| 2005/0209097 A1 | 9/2005 | Yang et al. | |
| 2005/0239636 A1 | 10/2005 | Gao et al. | |
| 2005/0288460 A1 | 12/2005 | Zhu et al. | |
| 2006/0154806 A1 | 7/2006 | Chen et al. | |
| 2006/0217261 A1 | 9/2006 | Morini et al. | |
| 2006/0287446 A1 | 12/2006 | Gao et al. | |
| 2008/0293897 A1 * | 11/2008 | Collina | C07F 3/003 526/124.2 |
| 2010/0099833 A1 | 4/2010 | Xia et al. | |

FOREIGN PATENT DOCUMENTS

| | | |
|---|---|---|
| CN | 1141285 | 1/1997 |
| CN | 1330086 | 1/2002 |
| CN | 1397568 | 2/2003 |
| CN | 1436766 | 8/2003 |
| CN | 1436796 | 8/2003 |
| CN | 1453298 | 11/2003 |
| CN | 1463990 | 12/2003 |
| CN | 1563112 | 1/2005 |
| CN | 1580136 | 2/2005 |
| CN | 1743347 | 3/2006 |
| CN | 101050245 | 10/2007 |
| CN | 100348624 | 11/2007 |
| CN | 101486722 | 7/2009 |
| CN | 101486776 | 7/2009 |
| EP | 0 113 960 A1 | 7/1984 |
| EP | 0 155 716 A1 | 9/1985 |
| EP | 0 395 083 B1 | 11/1997 |
| JP | 57030708 | 2/1982 |
| JP | 60203606 | 10/1985 |
| WO | WO 87/07620 | 12/1987 |
| WO | WO 93/11166 | 6/1993 |
| WO | WO 93/20115 | 10/1993 |
| WO | WO 01/036496 | 5/2001 |
| WO | WO 03/068723 | 8/2003 |
| WO | WO 03/068828 | 8/2003 |
| WO | WO 2011/006278 | 1/2011 |

* cited by examiner

SPHERICAL MAGNESIUM HALIDE ADDUCT, A CATALYST COMPONENT AND A CATALYST FOR OLEFIN POLYMERIZATION PREPARED THEREFROM

CROSS-REFERENCE TO RELATED APPLICATIONS

This is a divisional application of U.S. application Ser. No. 13/384,419, whose 35 U.S.C. § 371(c) filing date is Apr. 2, 2012, which is a national-stage filing of International Application No. PCT/CN2009/000796, filed Jul. 15, 2009.

FIELD OF THE INVENTION

The present invention relates to a spherical magnesium halide adduct, and to a catalyst component and a catalyst prepared from the adduct as support and being useful in olefin polymerization, in particular propylene polymerization. More specifically, the present invention relates to a spherical magnesium halide adduct comprising at least three components: a magnesium halide, an alcohol and an o-alkoxy benzoate compound, to a catalyst component comprising a reaction product of the adduct with a titanium compound and optionally an internal electron donor compound, and to the use of the catalyst component.

BACKGROUND OF THE INVENTION

The preparation of Ziegler-Natta catalysts by supporting a titanium compound and an electron donor compound on an active magnesium halide support is well known in the art.

An adduct of a magnesium halide and an alcohol is often used as the active magnesium halide support, and reacts with a titanium halide and an electron donor compound to give a spherical catalyst component, which, together with a cocatalyst and optionally an external electron donor compound, constitutes a catalyst. When used in olefin polymerization, in particular in propylene polymerization, such a catalyst exhibits a relatively high polymerization activity and a higher stereospecificity.

Known magnesium halide/alcohol adducts comprise generally binary components: magnesium dichloride and an alcohol. Some of known alcohol adducts further comprise a minor amount of water. Such alcohol adducts may be prepared by known processes, such as spray drying processes, spray cooling processes, high-pressure extruding processes, or high-speed stirring processes. The magnesium dichloride/alcohol adducts are described in, for example, U.S. Pat. No. 4,421,674, U.S. Pat. No. 4,469,648, WO 8707620, WO 9311166, U.S. Pat. No. 5,100,849, U.S. Pat. No. 6,020,279, U.S. Pat. No. 4,399,054, EP 0 395 083, U.S. Pat. No. 6,127,304 and U.S. Pat. No. 6,323,152.

It has been found that when the catalysts prepared from such a magnesium dichloride/alcohol adduct are used in olefin polymerization, a cracking phenomenon of catalyst particles as well as polymer particles takes place easily so that there are overmuch polymer fines. A main reason might be that catalytic active sites formed in the adduct supports by reacting the adducts with titanium halides and electron donor compounds are not uniformly distributed. In order to overcome this drawback, it has been attempted to introduce the electron donor compound during the preparation of the magnesium dichloride/alcohol adduct supports. For example, the technique as disclosed in Chinese Patent ZL02136543.1 and CN1563112A introduces an internal electron donor well-known in the art, such as a phthalate, in the preparation of the support so as to form a spherical "magnesium dichloride-alcohol-phthalate" multi-component support, which then reacts with titanium tetrachloride to form a catalyst component. However, because the spherical multi-component support is likely viscous during the preparation thereof, it is difficult to form spherical particles having a desired particle diameter (the disclosed spherical supports have average particle sizes, D50, in the range of from 70 to 200 microns). Furthermore, when used in propylene polymerization, the catalyst exhibits a catalytic activity of at most 406 gPP/gcat. Therefore, the catalyst is not satisfied.

Chinese patent application CN101050245A discloses a spherical adduct support having a general formula of $MgX_2 \cdot mROH \cdot nE \cdot pH_2O$, wherein E is a gem-dihydrocarbyloxy hydrocarbon compound. The support has a narrower particle size distribution and the average particle size of the support can be easily controlled. The catalyst component prepared by reacting the adduct support with a titanium compound has a good hydrogen response when used in olefin polymerization, in particular in propylene polymerization, and the resultant polymer has a good particle morphology. However, when the catalyst component is used in propylene polymerization at a higher hydrogen concentration, its stereospecificity, especially the isotacticity index of the obtained polymer having a higher melt index, needs to be further enhanced.

Chinese patent application CN85101441A discloses a process for the polymerization of an alpha monoolefin in the presence of certain supported coordination catalyst systems which comprise (a) a procatalyst, (b) a cocatalyst, and (c) a selectivity control agent, wherein (a) is a solid composition comprising magnesium dichloride, titanium tetrachloride, and an electron donor; (b) is an aluminium trialkyl; and (c) is a combination of a strong selectivity control agent and a weak selectivity control agent. Said strong selectivity control agent may be an alkoxy benzoate, preferably a p-alkoxy benzoate, and the weak selectivity control agent is an ether or a tertiary amine. However, in the case of propylene polymerization, the resultant polymers have lower isotacticity indices, when either the alkoxy benzoate alone or the combination of the strong selectivity control agent and the weak selectivity control agent is used.

Chinese patent application CN1743347A discloses the incorporation of o-alkoxybenzoate compounds as internal electron donor into olefin polymerization catalyst components. Said patent application discloses that, when a combination of an o-alkoxybenzoate compound and a phthalate compound is used as internal electron donor, the hydrogen response of the resultant catalyst can be improved. However, by using such a catalyst, the obtained polypropylene having a high melt index will have a lower isotacticity index.

Thus, there still need catalysts for olefin polymerization, which will exhibit a relatively high polymerization activity, a higher stereospecificity and the performance that can obtain higher isotactic index polypropylene with higher melt index at a higher hydrogen concentration, and which will give a polymer having a good particle morphology and a higher bulk density.

SUMMARY OF THE INVENTION

The inventors made diligently studies and, as a result, they have surprisingly found that incorporating an o-alkoxybenzoate compound, either formed in situ or added as such, into a magnesium halide/alcohol adduct support gives excellent results, in comparison with the case where no o-alkoxybenzoate compound is used or an o-alkoxybenzoate compound is introduced during the preparation of a solid catalyst component from a magnesium halide/alcohol adduct support. For example, the resultant supports have good particle morphology, and when used in olefin polymerization, especially in propylene polymerization, the catalysts prepared from such o-alkoxybenzoate-containing supports exhibit a relatively high stereospecificity, even at a higher hydrogen concentration provided for preparing a polymer having a higher melt index. Such a polymer having a higher melt index and a higher isotacticity index will have good mechanical properties and a good processibility, and thus is desired. Furthermore, when used in olefin polymerization, especially in propylene polymerization, the catalysts prepared from the o-alkoxybenzoate-containing supports exhibit higher polymerization activities, and the resulting polymers have good particle morphology and less fines so that the catalysts are quite suitable for the industrial scale production of polypropylene.

Thus, an object of the invention is to provide a spherical magnesium halide adduct comprising a magnesium halide, an alcohol and an o-alkoxybenzoate compound.

Another object of the invention is to provide a process for preparing the spherical magnesium halide adduct according to the invention.

Still another object of the invention is to provide a titanium-containing catalyst component for olefin polymerization, which comprises a reaction product of the spherical magnesium halide adduct of the invention, a titanium compound, and optionally an internal electron donor.

Still another object of the invention is to provide a catalyst for olefin polymerization, comprising a reaction product of
a) the titanium-containing catalyst component according to the invention;
b) an alkylaluminum cocatalyst; and
c) optionally, an external electron-donor.

Still another object of the invention is to provide a process for polymerizing olefin $CH_2=CHR$, in which R is H, or aryl or alkyl having 1 to 6 carbon atoms, comprising contacting the olefin(s) with the catalyst according to the invention under polymerization conditions.

DETAILED DESCRIPTION OF THE PREFERRED EMBODIMENTS

As used herein, the term "polymerization" intends to encompass homopolymerization and copolymerization.

As used herein, the term "polymer" intends to encompass homopolymer, copolymer and terpolymer.

As used herein, the term "catalyst component" intends to means main catalyst component or procatalyst, which, together with a conventional cocatalyst, for example an alkyl alumimium, and optionally an external electron donor compound, constitutes the catalyst for olefin polymerization.

As used herein, the term "catalyst" is synonymous with the term "catalyst system", and comprises a catalyst component, a cocatalyst, and optionally an external electron donor compound.

In the first aspect, the present invention provides a magnesium halide adduct represented by the following formula (I):

$$MgX_2 \cdot mROH \cdot nE \cdot pH_2O \quad (I)$$

in which X is chlorine, bromine, a $C_1$-$C_{12}$ alkoxy, a $C_3$-$C_{10}$ cycloalkoxy or a $C_6$-$C_{10}$ aryloxy, with the proviso that at least one X is chlorine or bromine; R is a $C_1$-$C_{12}$ alkyl, a $C_3$-$C_{10}$ cycloalkyl or a $C_6$-$C_{10}$ aryl; E is an o-alkoxybenzoate compound represented by the formula (II):

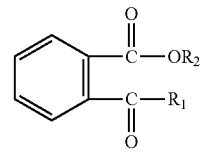

in which $R_1$ and $R_2$ groups are independently a $C_1$-$C_{12}$ linear or branched alkyl, a $C_3$-$C_{10}$ cycloalkyl, a $C_6$-$C_{10}$ aryl, a $C_7$-$C_{10}$ alkaryl or an $C_7$-$C_{10}$ aralkyl, the $R_1$ and $R_2$ groups are identical to or different from the R group;

m is in a range of from 1.0 to 5.0, preferably from 1.5 to 3.5;

n is in a range of from 0.001 to 0.5, preferably from 0.005 to 0.2; and p is in a range of from 0 to 0.8.

In the formula (I), X is preferably chlorine. Examples of the magnesium halide $MgX_2$ useful in the preparation of the magnesium halide adduct include, but are not limited to, magnesium dichloride, magnesium dibromide, phenoxy magnesium chloride, isopropoxy magnesium chloride, and butoxy magnesium chloride, with magnesium dichloride being preferred. The magnesium halides may be used alone or in combination.

The alcohols useful in the preparation of the magnesium halide adduct may be represented by a formula ROH, wherein R is a $C_1$-$C_{12}$ alkyl, a $C_3$-$C_{10}$ cycloalkyl or a $C_6$-$C_{10}$ aryl, preferably a $C_1$-$C_4$ alkyl. Examples of the alcohols include, but are not limited to, methanol, ethanol, n-propanol, iso-propanol, n-butanol, iso-butanol, n-pentanol, iso-pentanol, n-hexanol, n-octanol, 2-ethylhexanol, ethylene glycol and propylene glycol.

In the formula (II), $R_1$ and $R_2$ are independently a $C_1$-$C_{12}$ linear or branched alkyl, a $C_3$-$C_{10}$ cycloalkyl, a $C_6$-$C_{10}$ aryl, a $C_7$-$C_{10}$ alkaryl or a $C_7$-$C_{10}$ aralkyl, such as methyl, ethyl, propyl, isopropyl, butyl, iso-butyl, t-butyl, pentyl, hexyl, iso-pentyl, cyclopentyl, cyclohexyl, phenyl, tolyl, indenyl, benzyl or phenyl ethyl. Preferably, $R_1$ and $R_2$ are independently a $C_1$-$C_6$ linear or branched alkyl, a $C_3$-$C_6$ cycloalkyl, or a $C_6$-$C_{10}$ aryl. More preferably, $R_1$ and $R_2$ are independently methyl, ethyl, propyl, isopropyl, butyl, iso-butyl, t-butyl, or pentyl.

Examples of the o-alkoxybenzoate compounds represented by the formula (II) include methyl o-methoxybenzoate, ethyl o-methoxybenzoate, n-propyl o-methoxybenzoate, isopropyl o-methoxybenzoate, n-butyl o-methoxybenzoate, isobutyl o-methoxybenzoate, methyl o-ethoxybenzoate, ethyl o-ethoxybenzoate, n-propyl o-ethoxybenzoate, isopropyl o-ethoxybenzoate, n-butyl o-ethoxybenzoate, and isobutyl o-methoxybenzoate.

In a preferred embodiment, the magnesium halide adduct according to the invention has a composition represented by the formula (I), $$MgX_2 \cdot mROH \cdot nE \cdot pH_2O \quad (I)$$

wherein X is chlorine; R is a $C_1$-$C_4$ alkyl; m is in a range of from 1.5 to 3.5; n is in a range of from 0.005 to 0.2; E is an o-alkoxybenzoate compound represented by the formula (II):

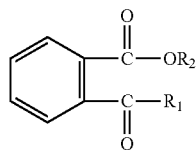

in which $R_1$ is methyl, ethyl, n-propyl, isopropyl, n-butyl or iso-butyl; $R_2$ is identical to or different from R, and is methyl, ethyl, n-propyl, isopropyl, n-butyl, or iso-butyl; and p is as defined above.

The above adduct may be prepared by processes well-known in the art, such as spray drying processes, spray cooling processes, high-pressure extruding processes, high-speed stirring processes, or super-gravity rotary bed processes (such as the process as described in CN1580136A).

In general, a magnesium halide, an alcohol, and an o-alkoxybenzoate or its precursor, e.g., o-alkoxy benzoyl halide, such as chloride, react at first with each other in the presence or in the absence of an inert liquid medium at an elevated temperature, with the final temperature being high enough to melt the reaction mixture, and preferably in the range of from 100° C. to 140° C. The inert liquid medium is generally an inert aliphatic hydrocarbon solvent, such as kerosene, paraffin oil, vaseline oil, white oil, hexane, and heptane, and when necessary, contains optionally an organic silicon compound, such as an organic silicon oil, for example, dimethyl silicone oil or the like, and/or a surfactant. Then the resulting melt is solidified in a cooling medium to form solid particles, wherein the cooling medium may be an inert hydrocarbon solvent having a relatively low boiling point, such as pentane, hexane, heptane, gasoline, petroleum ether, and the like, and may be controlled at a temperature of from −60° C. to 30° C., preferably from −40° C. to 0° C., prior to its contacting with the magnesium halide adduct melt stream.

In a preferred embodiment, the magnesium halide adduct according to the invention may be prepared by a process comprising the steps of (i) preparing a melt of a magnesium halide adduct by:
in a closed reactor, mixing the magnesium halide, the alcohol, the o-alkoxybenzoate or its precursor (e.g., o-alkoxy benzoyl halide, such as chloride) and an inert liquid medium, and heating the resultant mixture to a temperature of from 100 to 140° C. while stirring, to form a melt of a magnesium halide adduct, wherein the magnesium halide is added in an amount of from 0.1 to 1.0 mol/liter of the inert liquid medium, and the alcohol and the o-alkoxybenzoate or its precursor are added in an amount of from 1 to 5 moles and from 0.001 to 0.5 moles, respectively, with respect to one mole of the magnesium halide;

wherein the inert liquid medium is as described above; and wherein a trace amount of water contained in the magnesium halide and/or the alcohol may participate in the reaction for forming the adduct; and in the preparation of the magnesium halide adduct, the order of the addition of individual raw materials is arbitrary; and (ii) forming spherical particles of the magnesium halide adduct by:

applying shearing action on the above melt of the magnesium halide adduct and then discharging it into a cooling medium, to form spherical particles of the magnesium halide adduct, wherein the application of the shearing action may be accomplished by a conventional method, such as a high-speed stirring process (see, for example, CN 1330086), a spraying process (see, for example, U.S. Pat. No. 6,020,279), a super-gravity rotary bed process (see, for example, CN 1580136A), or an emulsification apparatus process (see, for example, CN 1463990A);

wherein the cooling medium is as described above.

After washed with an inert hydrocarbon solvent and dried, the above-prepared spherical adduct particles may be used in the preparation of catalyst components for olefin polymerization.

In the second aspect, the present invention provides a titanium-containing catalyst component for olefin polymerization, which comprises a reaction product of (1) the spherical magnesium halide adduct of the invention, (2) a titanium compound, and optionally (3) an internal electron donor compound.

The titanium compound may be selected from those represented by formula $TiX_3$ or $Ti(OR^3)_{4-m}X_m$, in which $R^3(s)$ is/are independently $C_1$-$C_{14}$ aliphatic hydrocarbyl group, X(s) is/are independently F, Cl, Br or I, and m is an integer of from 1 to 4. Examples of the titanium compound include, but are not limited to, titanium tetrachloride, titanium tetrabromide, titanium tetraiodide, tetrabutoxy titanium, tetraethoxy titanium, tributoxy titanium chloride, dibutoxy titanium dichloride, butoxy titanium trichloride, triethoxy titanium chloride, diethoxy titanium dichloride, ethoxy titanium trichloride, titanium trichloride, and mixtures thereof, with titanium tetrachloride being preferred.

The titanium-containing catalyst component for olefin polymerization according to the invention may be prepared by methods known in the art, for example, by reacting the particulate magnesium halide adduct with a titanium compound. In a preferred embodiment, the titanium-containing catalyst component is prepared by a method comprising the steps of: suspending the magnesium halide adduct of the invention in chilled titanium tetrachloride or a mixture of titanium tetrachloride and an inert solvent, with the temperature of the liquid being generally in a range of from −30° C. to 0° C., preferably from −20° C. to −10° C.; then heating the resulting mixture to a temperature of from 40° C. to 130° C., preferably from 60° C. to 120° C., and maintaining at that temperature for 0.5 to 2.0 hours; and then filtering off the liquid and recovering the solids. Such a treatment with titanium tetrachloride may be performed for one or more times, and preferably for 2 to 4 times. The inert solvent is preferably an aliphatic or aromatic hydrocarbon, such as hexane, heptane, octane, decane, toluene, and the like.

Before, during or after the reaction between the magnesium halide adduct and the titanium compound, at least one internal electron donor compound may optionally be used to treat the magnesium halide adduct. Use of internal electron donor compounds in catalyst components for olefin polymerization is well known in the art. In particular, the incorporation of an internal electron donor compound in a catalyst component for propylene polymerization may be quite necessary, in order to obtain propylene polymers having high isotacticity indices. All internal electron-donor compounds commonly used in the art can be used in the present invention.

Suitable internal electron donor compounds include esters, ethers, ketones, amines, silanes, and the like. Esters of aliphatic and aromatic mono- and poly-basic carboxylic acids, esters of diols, and di-ethers are preferred.

Specific esters of aliphatic and aromatic mono- and poly-basic carboxylic acids include, for example, benzoates, phthalates, malonates, succinates, glutarates, pivalates, adipates, sebacates, maleates, naphthalene dicarboxylates, trimellitates, benzene-1,2,3-tricarboxylates, pyromellitates and carbonates. Examples include ethyl benzoate, diethyl phthalate, di-iso-butyl phthalate, di-n-butyl phthalate, di-iso-octyl phthalate, di-n-octyl phthalate, diethyl malonate, dibutyl malonate, diethyl 2,3-di-iso-propylsuccinate, di-iso-butyl 2,3-di-isopropylsuccinate, di-n-butyl 2,3-diisopropylsuccinate, dimethyl 2,3-di-isopropylsuccinate, di-iso-butyl 2,2-dimethylsuccinate, di-iso-butyl 2-ethyl-2-methylsuccinate, diethyl 2-ethyl-2-methylsuccinate, diethyl adipate, dibutyl adipate, diethyl sebacate, dibutyl sebacate, diethyl maleate, di-n-butyl maleate, diethyl naphthalene dicarboxylate, dibutyl naphthalene dicarboxylate, triethyl trimellitate, tributyl trimellitate, triethyl benzene-1,2,3-tricarboxylate, tributyl benzene-1,2,3-tricarboxylate, tetraethyl pyromellitate, tetrabutyl pyromellitate, etc.

Specific ester compounds of diols include those represented by the formula (III)

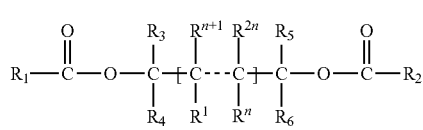

(III)

wherein $R_1$ to $R_6$ and $R^1$ to $R^{2n}$, which are identical or different, are hydrogen, halogen, or optionally substituted linear or branched $C_1$-$C_{20}$ alkyl, $C_3$-$C_{20}$ cycloalkyl, $C_6$-$C_{20}$ mono-ring or multi-ring aryl, $C_7$-$C_{20}$ alkylaryl, $C_7$-$C_{20}$ arylalkyl, $C_2$-$C_{10}$ alkenyl, or $C_2$-$C_{10}$ ester group, with the proviso that $R_1$ and $R_2$ are not hydrogen, $R_3$ to $R_6$ and $R^1$ to $R^{2n}$ optionally comprise one or more heteroatoms, which are selected from the group consisting of nitrogen, oxygen, sulfur, silicon, phosphorus and halogen, replacing for carbon or hydrogen or the both, and one or more of $R_3$ to $R_6$ and $R^1$ to $R^{2n}$ may be linked to form a ring; and n is an integer ranging from 0 to 10, as disclosed in CN1436766, all relevant contents of which are incorporated herein by reference.

Among said ester compounds of diols, the preferred are compounds of the formula (IV),

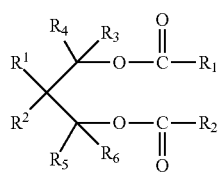

(IV)

wherein $R_1$ to $R_6$, $R^1$ and $R^2$ are as defined for the formula (III), and compounds of the formula (V):

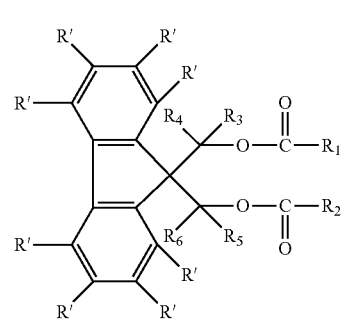

(V)

wherein $R_1$-$R_6$ groups are as defined for the formula (III); R's are identical or different, and represent hydrogen, halogen, linear or branched $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl.

Examples of ester compounds of diols include: propan-1,3-diol dibenzoate, 2-methyl-propan-1,3-diol dibenzoate, 2-ethyl-propan-1,3-diol dibenzoate, 2-propyl-propan-1,3-diol dibenzoate, 2-butyl-propan-1,3-diol dibenzoate, 2,2-dimethyl-propan-1,3-diol dibenzoate, (R)-1-phenyl-propan-1,3-diol dibenzoate, (S)-1-phenyl-propan-1,3-diol dibenzoate, 1,3-diphenyl-propan-1,3-diol dibenzoate, 1,3-diphenyl-2-methyl-propan-1,3-diol dibenzoate, 1,3-diphenyl-propan-1,3-diol dipropionate, 1,3-diphenyl-2-methyl-propan-1,3-diol dipropionate, 1,3-diphenyl-2-methyl-propan-1,3-diol diacetate, 1,3-diphenyl-2,2-dimethyl-propan-1,3-diol dibenzoate, 1,3-diphenyl-2,2-dimethyl-propan-1,3-diol dipropionate, 1,3-di-tert-butyl-2-ethyl-propan-1,3-diol dibenzoate, 1,3-diphenyl-propan-1,3-diol diacetate, 1,3-diisopropyl-propan-1,3-diol di(4-butylbenzoate), 2-amino-1-phenyl-propan-1,3-diol dibenzoate, 2-methyl-1-phenyl-butan-1,3-diol dibenzoate, 2-methyl-1-phenyl-butan-1,3-diol dipivalate, 3-butyl-pentan-2,4-diol dibenzoate, 3,3-dimethyl-pentan-2,4-diol dibenzoate, (2S,4S)-(+)-pentan-2,4-diol dibenzoate, (2R,4R)-(+)-pentan-2,4-diol dibenzoate, pentan-2,4-diol di(p-chlorobenzoate), pentan-2,4-diol di(m-chlorobenzoate), pentan-2,4-diol di(p-bromobenzoate), pentan-2,4-diol di(o-bromobenzoate), pentan-2,4-diol di(p-methylbenzoate), pentan-2,4-diol di(p-tert-butylbenzoate), pentan-2,4-diol di(p-butylbenzoate), 2-methyl-pentan-1,3-diol dibenzoate, 2-methyl-pentan-1,3-diol di(p-chlorobenzoate), 2-methyl-pentan-1,3-diol di(p-methylbenzoate), 2-butyl-pentan-1,3-diol di(p-methylbenzoate), 2-methyl-pentan-1,3-diol di(p-tert-butylbenzoate), 2-methyl-pentan-1,3-diol dipivalate, 2-methyl-pentan-1,3-diol dibenzoate, 2-ethyl-pentan-1,3-diol dibenzoate, 2-propyl-pentan-1,3-diol dibenzoate, 2-allyl-pentan-1,3-diol dibenzoate, 2-butyl-pentan-1,3-diol dibenzoate, pentan-1,3-diol di(p-chlorobenzoate), pentan-1,3-diol di(m-chlorobenzoate), pentan-1,3-diol di(p-bromobenzoate), pentan-1,3-diol di(o-bromobenzoate), pentan-1,3-diol di(p-methylbenzoate), pentan-1,3-diol di(p-tert-butylbenzoate), pentan-1,3-diol di(p-butylbenzoate), pentan-1,3-diol monobenzoate monocinnamate, pentan-1,3-diol dicinnamate, pentan-1,3-diol dipropionate, 2-methyl-pentan-1,3-diol monobenzoate monocinnamate, 2,2-dimethyl-pentan-1,3-diol dibenzoate, 2,2-dimethyl-pentan-1,3-diol monobenzoate monocinnamate, 2-methyl-pentan-1,3-diol monobenzoate monocinnamate, 2,2,4-trimethyl-pentan-1,3-diol dibenzoate, 2,2,4-trimethyl-pentan-1,3-diol di(isopropyl-formate), 1-trifluoromethyl-3-methyl-pentan-2,4-diol dibenzoate, pentan-2,4-diol di(p-fluoromethylbenzoate), pentan-2,4-diol di(2-furancarboxylate), 3-butyl-3-methyl-pentan-2,4-diol dibenzoate, 2-ethyl-hexan-1,3-diol dibenzoate, 2-propyl-hexan-1,3-diol dibenzoate, 2-butyl-hexan-1,3-diol dibenzoate, 4-ethyl-hexan-1,3-diol dibenzoate, 4-methyl-hexan-1,3-diol dibenzoate, 3-methyl-hexan-1,3-diol dibenzoate, 3-ethyl-hexan-1,3-diol dibenzoate, 2,2,4,6,6-pentamethyl-hexan-3,5-diol dibenzoate, hepta-6-en-2,4-diol dibenzoate, 2-methyl-hepta-6-en-2,4-diol dibenzoate, 3-methyl-hepta-6-en-2,4-diol dibenzoate, 4-methyl-hepta-6-en-2,4-diol dibenzoate, 5-methyl-hepta-6-en-2,4-diol dibenzoate, 6-methyl-hepta-6-en-2,4-diol dibenzoate, 3-ethyl-hepta-6-en-2,4-diol dibenzoate, 4-ethyl-hepta-6-en-2,4-diol dibenzoate, 5-ethyl-hepta-6-en-2,4-diol dibenzoate, 6-ethyl-hepta-6-en-2,4-diol dibenzoate, 3-propyl-hepta-6-en-2,4-diol dibenzoate, 4-propyl-hepta-6-en-2,4-diol dibenzoate, 5-propyl-hepta-6-en-2,4-diol dibenzoate, 6-propyl-hepta-6-en-2,4-diol dibenzoate, 3-butyl-hepta-6-en-2,4-diol dibenzoate, 4-butyl-hepta-6-en-2,4-diol dibenzoate, 5-butyl-hepta-6-en-2,4-diol dibenzoate, 6-butyl-hepta-6-en-2,4-diol dibenzoate, 3,5-dimethyl-hepta-6-en-2,4-diol dibenzoate, 3,5-diethyl-hepta-6-en-2,4-diol dibenzoate, 3,5-propyl-hepta-6-en-2,4-diol dibenzoate, 3,5-dibutyl-hepta-6-en-2,4-diol dibenzoate, 3,3-dimethyl-hepta-6-en-2,4-diol dibenzoate, 3,3-diethyl-hepta-6-en-2,4-diol dibenzoate, 3,3-dipropyl-hepta-6-en-2,4-diol dibenzoate, 3,3-dibutyl-hepta-6-en-2,4-diol dibenzoate, 3-ethyl-heptan-3,5-diol dibenzoate, 4-ethyl-heptan-3,5-diol dibenzoate, 5-ethyl-heptan-3,5-diol dibenzoate, 3-propyl-heptan-3,5-diol dibenzoate, 4-propyl-heptan-3,5-diol dibenzoate, 3-butyl-heptan-3,5-diol dibenzoate, 2,3-dimethyl-heptan-3,5-diol dibenzoate, 2,4-dimethyl-heptan-3,5-diol dibenzoate, 2,5-dimethyl-heptan-3,5-diol dibenzoate, 2,6-dimethyl-heptan-3,5-diol dibenzoate, 3,3-dimethyl-heptan-3,5-diol dibenzoate, 4,4-dimethyl-heptan-3,5-diol dibenzoate, 4,5-dimethyl-heptan-3,5-diol dibenzoate, 4,6-dimethyl-heptan-3,5-diol dibenzoate, 4,4-dimethyl-heptan-3,5-diol dibenzoate, 6,6-dimethyl-heptan-3,5-diol dibenzoate, 3-ethyl-2-methyl-heptan-3,5-diol dibenzoate, 4-ethyl-2-methyl-heptan-3,5-diol dibenzoate, 5-ethyl-2-methyl-heptan-3,5-diol dibenzoate, 3-ethyl-3-methyl-heptan-3,5-diol dibenzoate, 4-ethyl-3-methyl-heptan-3,5-diol dibenzoate, 5-ethyl-3-methyl-heptan-3,5-diol dibenzoate, 3-ethyl-4-methyl-heptan-3,5-diol dibenzoate, 4-ethyl-4-methyl-heptan-3,5-diol dibenzoate, 9,9-bis(benzoyloxymethyl)fluorene, 9,9-bis((m-methoxybenzoyloxy)methyl)fluorene, 9,9-bis((m-chlorobenzoyloxy)methyl)fluorene, 9,9-bis((p-chlorobenzoyloxy)methyl)fluorene, 9,9-bis(cinnamoyloxymethyl)fluorene, 9-(benzoyloxymethyl)-9-(propionyloxymethyl)fluorene, 9,9-bis(pripionyloxymethyl)fluorene, 9,9-bis(acryloxymethyl)fluorene, 9,9-bis(pivaloyloxymethyl)fluorene, etc.

Such ester compounds of diols are disclosed in detail in CN1453298A, CN1436796A, CN1436766A, WO 03/068828 and WO 03/068723, all relevant contents of which are incorporated herein by reference.

The preferred ether compounds include 1,3-diether compounds represented by the formula (VI):

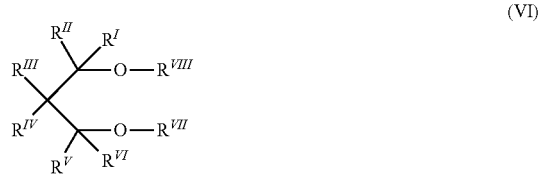
(VI)

wherein $R^I$, $R^{II}$, $R^{III}$, $R^{IV}$, $R^V$ and $R^{VI}$ are independently selected from the group consisting of hydrogen, halogen, linear or branched $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl; $R^{VII}$ and $R^{VIII}$ are independently selected from the group consisting of linear or branched $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl; and two or more of $R^I$ to $R^{VI}$ groups are optionally bonded to each other to form a ring. Those 1,3-diethers wherein $R^{VII}$ and $R^{VIII}$ are independently $C_1$-$C_4$ alkyl are preferred.

Examples of di-ether compounds include: 2-(2-ethyl hexyl)-1,3-dimethoxypropane, 2-isopropyl-1,3-dimethoxypropane, 2-butyl-1,3-dimethoxypropane, 2-sec-butyl-1,3-dimethoxypropane, 2-cyclohexyl-1,3-dimethoxypropane, 2-phenyl-1,3-dimethoxypropane, 2-(2-phenylethyl)-1,3-dimethoxypropane, 2-(2-cyclohexylethyl)-1,3-dimethoxypropane, 2-(p-chlorophenyl)-1,3-dimethoxypropane, 2-(diphenylmethyl)-1,3-dimethoxypropane, 2,2-di-cyclohexyl-1,3-dimethoxypropane, 2,2-di-cyclopentyl-1,3-dimethoxypropane, 2,2-di-ethyl-1,3-di-methoxypropane, 2,2-di-propyl-1,3-di-methoxypropane, 2,2-di-isopropyl-1,3-di-methoxypropane, 2,2-di-butyl-1,3-di-methoxypropane, 2-methyl-2-propyl-1,3-di-methoxypropane, 2-methyl-2-benzyl-1,3-di-methoxypropane, 2-methyl-2-ethyl-1,3-di-methoxypropane, 2-methyl-2-isopropyl-1,3-di-methoxypropane, 2-methyl-2-phenyl-1,3-di-methoxypropane, 2-methyl-2-cyclohexyl-1,3-di-methoxypropane, 2,2-di(2-cyclohexyl ethyl)-1,3-di-methoxypropane, 2-methyl-2-iso-butyl-1,3-di-methoxypropane, 2-methyl-2-(2-ethyl hexyl)-1,3-di-methoxypropane, 2,2-di-iso-butyl-1,3-di-methoxypropane, 2,2-di-phenyl-1,3-di-methoxypropane, 2,2-di-benzyl-1,3-di-methoxypropane, 2,2-di(cyclohexyl methyl)-1,3-di-methoxypropane, 2-iso-butyl-2-isopropyl-1,3-di-methoxypropane, 2-(1-methyl butyl)-2-isopropyl-1,3-di-methoxypropane, 2-isopropyl-2-iso-pentyl-1,3-di-methoxypropane, 2-phenyl-2-isopropyl-1,3-di-methoxypropane, 2-phenyl-2-sec-butyl-1,3-di-methoxypropane, 2-benzyl-2-isopropyl-1,3-di-methoxypropane, 2-cyclopentyl-2-isopropyl-1,3-di-methoxypropane, 2-cyclopentyl-2-sec-butyl-1,3-di-methoxypropane, 2-cyclohexyl-2-isopropyl-1,3-di-methoxypropane, 2-cyclohexyl-2-sec-butyl-1,3-di-methoxypropane, 2-isopropyl-2-sec-butyl-1,3-di-methoxypropane, 2-cyclohexyl-2-cyclohexyl methyl-1,3-di-methoxypropane, etc.

Such di-ether compounds are disclosed in detail in CN1020448C, CN 100348624C and CN1141285A, all relevant contents of which are incorporated herein by reference.

In the preparation of the titanium-containing catalyst component according to the invention, the titanium compound is used in an amount of from 5 to 50 moles, with respect to one mole of magnesium halide in the magnesium halide adduct; and the internal electron donor compound is used in an amount of from 0 to 0.8 moles, preferably from 0.01 to 0.5 moles, with respect to one mole of magnesium halide in the magnesium halide adduct.

In the third aspect, the present invention provides a catalyst for olefin polymerization, comprising a reaction product of the following components:

a) the titanium-containing catalyst component according to the present invention (active component);

b) an alkylaluminum compound as a cocatalyst, represented by a formula $AlR''_nX_{3-n}$, wherein $R''$(s) is/are independently $C_1$-$C_8$ linear, branched or cyclic alkyl; X(s) is/are independently halogen, preferably chlorine; and n=1, 2 or 3. The preferred are triethyl aluminum, triisobutyl aluminum, tri-n-butyl aluminum, tri-n-hexyl aluminum, tri-n-octyl aluminum, alkyl aluminum chlorides, such as $AlEt_2Cl$, etc. These alkylaluminum compounds can be used alone or in combination. In general, the alkylaluminum compound(s) is/are used in such an amount that molar ratio of Al/Ti is in a range of from 1 to 1000; and c) optionally, an external electron donor compound, such as mono- or multi-functional carboxylic acids, carboxylic anhydrides, esters of carboxylic acids, ketones, ethers, alcohols, lactones, organic phosphorus compounds, and organic silicon compounds, in an amount ranging from 0.005 to 0.5 moles, preferably from 0.01 to 0.25 moles, with respect to one mole of the alkylaluminum compound.

Preferred external electron donor compounds include silicon compounds of formula $R^1{}_aR^2{}_bSi(OR^3)_c$, wherein a and b are independently an integer of from 0 to 2, c is an integer of from 1 to 3, and the sum of (a+b+c) is 4; $R^1$, $R^2$ and $R^3$ are independently $C_1$-$C_{18}$ hydrocarbyl optionally containing heteroatom(s). Among these silicon compounds, those wherein a is 1, b is 1, c is 2, at least one of $R^1$ and $R^2$ is selected from the group consisting of branched alkyl, alkenyl, cycloalkyl or aryl having 3 to 10 carbon atoms and optionally containing heteroatom(s), and $R^3$ is a $C_1$-$C_{10}$ alkyl, especially methyl, are particularly preferred. Examples of such silicon compounds include cyclohexyl methyl dimethoxy silane, diisopropyl dimethoxy silane, di-n-butyl dimethoxy silane, di-iso-butyl dimethoxy silane, diphenyl dimethoxy silane, methyl tert-butyl dimethoxy silane, dicyclopentyl dimethoxy silane, 2-ethylpiperidino tert-butyl dimethoxy silane, 1,1,1-trifluoro-propan-2-yl 2-ethylpiperidino dimethoxy silane and 1,1,1-trifluoro-propan-2-yl methyl dimethoxy silane. Additionally, those silicon compounds wherein a is 0, c is 3, $R^2$ is a branched alkyl or cycloalkyl optionally containing heteroatom(s), and $R^3$ is methyl are also preferred. Examples of such silicon compounds include cyclohexyl trimethoxy silane, tert-butyl trimethoxy silane and tert-hexyl trimethoxy silane.

The alkyl aluminium cocatalyst b) and the optional external electron donor compound c) can contact and react with the active component a) separately or as a mixture.

The catalyst of the invention is useful in the polymerization of olefin $CH_2$=CHR (wherein R is H, or alkyl or aryl having 1 to 6 carbon atoms) or a feed containing said olefin and a small amount of diene, if necessary.

Thus, in the fourth aspect, the present invention provides a process for polymerizing olefin, comprising contacting an olefin of formula $CH_2$=CHR, wherein R is H, or aryl or alkyl having 1 to 6 carbon atoms, and optionally another kind of said olefin as comonomer, and optionally a diene as a second comonomer, with the catalyst of the invention under polymerization conditions.

The polymerization of olefin(s) can be carried out in liquid phase of the liquid olefin monomer(s) or a solution of the olefin monomer(s) in an inert solvent, or in gas phase, or in a combination of gas phase and liquid phase, according to the processes known per se. The polymerization is generally carried out at a temperature of from 0° C. to 150° C., preferably from 60° C. to 100° C., and at a normal or higher pressure.

EXAMPLES

The following examples are provided to further illustrate the present invention and by no means intend to limit the scope thereof.

Testing Methods:

1. Melt index of polymers: ASTM D 1238-99.
2. Isotacticity index of polymers: measured by heptane extraction method carried out as follows: 2 g of a dry polymer sample is extracted with boiling heptane in an extractor for 6 hours, then the residual substance is dried to constant weight, and the ratio of the weight of the residual polymer (g) to 2 is regarded as isotacticity index.
3. Particle size distribution: average particle size and particle size distribution of the particulate magnesium halide adducts are measured on Masters Sizer Model 2000 (manufactured by Malvern Instruments Co., Ltd.).

Example 1

A. Preparation of Magnesium Dichloride Adduct

To a 500 ml reactor were charged with 150 ml of white oil (having a viscosity of 20-25 $mm^2$/s at 25° C., obtained from Hengshun Petroleum and Chemical Corp., Fushun, Liaoning), 30 g of magnesium dichloride, 50 ml of ethanol and 3 ml of o-methoxybenzoyl chloride. The mixture was heated to 125° C. while stirring at 500 rpm and maintained at that temperature for 2.5 hours. Then the mixture was added into 300 ml of dimethyl silicone oil (having a viscosity of 250-350 $mm^2$/s at 25° C., obtained from the Second Chemical Factory of Beijing, Beijing) preheated to 120° C. in a 1000 ml reactor, and stirred at 1600 rpm for 15 min. Then the mixture was discharged into 2 liters of hexane which had previously been cooled to −30° C. in a 3000 ml reactor. After filtering off the liquid, the solid was washed with hexane for five times and then dried under vacuum, to give 50 g of spherical magnesium dichloride adduct, the D50 of which was 75 microns.

B. Preparation of Catalyst Component

To a 300 ml glass reactor was charged with 100 ml of titanium tetrachloride, and the content was cooled to −20° C. Then 8 g of the above-prepared spherical magnesium dichloride adduct was added to the reactor, and the mixture was stirred at −20° C. for 30 min and then heated to 110° C. over 3 hours, with 1.5 ml of di-iso-butyl phthalate being added thereto when the temperature inside the reactor reached 20° C. Then the mixture was maintained at 110° C. for 0.5 hours, followed by filtering off the liquid. To the reactor containing the residual solids was added with 80 ml of titanium tetrachloride, the content was heated to 120° C. and maintained at that temperature for 30 min, and then the liquid was filtered off. The titanium tetrachloride treatment was repeated once. Then the residual solids was washed with hexane at 60° C. (80 ml×5), and then dried under vacuum, to give a spherical catalyst component.

C. Propylene Polymerization

To a 5 L autoclave were added 2.5 liters of propylene, 1 mmol of triethyl aluminium, 0.05 mmol of cyclohexyl methyl dimethoxy silane (CHMMS), 10 mg of the above spherical catalyst component, and 1.5 liters (standard volume) of hydrogen. Then the content was heated to 70° C. and allowed to polymerize for 1 hour. The results are shown in the Table 1 and Table 2 below.

Example 2

Following the procedure as described in Example 1.C, propylene polymerization was carried out by using the catalyst component prepared in Example 1, except for that the amount of hydrogen was changed to 5.0 liters (standard volume). The results are shown in the Table 1 and Table 2 below.

Example 3

Following the procedure as described in Example 1.C, propylene polymerization was carried out by using the catalyst component prepared in Example 1, except for that the amount of hydrogen was changed to 8.0 liters (standard volume). The results are shown in the Table 1 and Table 2 below.

Comparative Example 1

The procedure as described in Example 1 was repeated, except for that the o-methoxybenzoyl chloride was not used in the preparation of the magnesium halide adduct. The results are shown in the Table 1 and Table 2 below.

Comparative Example 2

Following the procedure as described in Example 1.C, propylene polymerization was carried out by using the catalyst component prepared in Comparative Example 1, except for that the amount of hydrogen was changed to 5.0 liters (standard volume). The results are shown in the Table 1 below.

Comparative Example 3

Following the procedure as described in Example 1.C, propylene polymerization was carried out by using the catalyst component prepared in Comparative Example 1, except for that the amount of hydrogen was changed to 8.0 liters (standard volume). The results are shown in the Table 1 below.

Example 4

The procedure as described in Example 1 was repeated, except for that 1,3-dimethyl-1,3-propandiol dibenzoate was used to replace for the di-iso-butyl phthalate in the preparation of the catalyst component. The results are shown in the Table 1 and Table 2 below.

Example 5

Following the procedure as described in Example 1.C, propylene polymerization was carried out by using the catalyst component prepared in Example 4, except for that the amount of hydrogen was changed to 5.0 liters (standard volume). The results are shown in the Table 1 and Table 2 below.

Comparative Example 4

The procedure as described in Comparative Example 1 was repeated, except for that 1,3-dimethyl-1,3-propandiol dibenzoate was used to replace for the di-iso-butyl phthalate in the preparation of the catalyst component. The results are shown in the Table 1 below.

Comparative Example 5

Following the procedure as described in Example 1.C, propylene polymerization was carried out by using the catalyst component prepared in Comparative Example 4, except for that the amount of hydrogen was changed to 5.0 liters (standard volume). The results are shown in the Table 1 below.

Comparative Example 6

A. Preparation of Magnesium Dichloride Adduct

A magnesium dichloride adduct was prepared by following the procedure as described in Example 1.A, except for that o-methoxybenzoyl chloride was replaced with 2,2-dimethoxypropane.

B. Preparation of Catalyst Component

A spherical catalyst component was prepared by following the procedure as described in Example 1.B, except for that the magnesium dichloride adduct prepared above was used as the support.

C. Propylene Polymerization

Following the procedure as described in Example 1.C, propylene polymerizations were carried out by using the catalyst component prepared above, with the amount of hydrogen, however, being 1.5 liters (standard volume), 5.0 liters (standard volume), and 8.0 liters (standard volume), respectively. The results are shown in the Table 1 below.

Comparative Example 7

A catalyst component was prepared by following the procedure as described in Comparative Example 1, steps A and B, except for that ethyl o-methoxybenzoate was used to replace for the di-iso-butyl phthalate in the preparation of the catalyst component.

Following the procedure as described in Example 1.C, propylene polymerizations were carried out by using the catalyst component prepared above, with the amount of hydrogen, however, being 5.0 liters (standard volume), and 8.0 liters (standard volume), respectively. The results are shown in the Table 1 below.

TABLE 1

Performance of the catalysts

| Example No. | Hydrogen added in polymerization (L) | Polymerization activity (kgPP/gcat.) | Isotacticity index of polymer (%) | MI of polymer (g/10 min) |
|---|---|---|---|---|
| Example 1 | 1.5 | 41.1 | 98.5 | 3.4 |
| Example 2 | 5.0 | 48.4 | 97.8 | 21 |
| Example 3 | 8.0 | 42.2 | 97.4 | 40 |
| Comparative Example 1 | 1.5 | 48.2 | 98.2 | 2.9 |
| Comparative Example 2 | 5.0 | 48.4 | 97.1 | 21 |
| Comparative Example 3 | 8.0 | 48.9 | 96.4 | 39 |
| Example 4 | 1.5 | 48.8 | 98.4 | 1.2 |
| Example 5 | 5.0 | 59.6 | 97.1 | 11 |
| Comparative Example 4 | 1.5 | 58.7 | 97.2 | 0.5 |
| Comparative Example 5 | 5.0 | 61.1 | 95.3 | 11 |
| Comparative Example 6 | 1.5 | 44.7 | 98.8 | 4.9 |
|  | 5.0 | 46.6 | 96.8 | 26 |
|  | 8.0 | 50.0 | 95.9 | 45 |
| Comparative Example 7 | 5.0 | 35.6 | 85.06 | 45 |
|  | 8.0 | 33.6 | 83.86 | 89 |

From the data shown in Table 1, it can be seen that, where an ester of aromatic carboxylic acid is used as internal electron donor (Examples 1, 2, 3 and Comparative Examples 1, 2, 3, 6), the catalysts according to the invention give polymers having a markedly enhanced isotacticity index, in particular in the case where the polymers have a higher melt index. That is to say, with the catalysts according to the invention, the resulting polymers having a higher melt index still have a higher isotacticity index. It can be seen from Table 1 that, where an ester of diol is used as internal electron donor (Examples 4, 5 and Comparative Examples 4, 5), the catalysts according to the invention give polymers having a more markedly enhanced isotacticity index.

From the results of Examples 2 and 3 as well as Comparative Example 7 shown in Table 1, it can be seen that, when an o-alkoxybenzoate compound is introduced as internal electron donor during the preparation of a catalyst component, the resultant catalyst has a markedly lower stereospecificity and a lower activity, while the catalysts according to the invention, which are prepared by introducing the o-alkoxybenzoate compound, either formed in situ or as such, into the support of the catalyst components, have a relatively higher stereospecificity in propylene polymerization.

TABLE 2

| | Particle size distribution of polymers | | | | |
|---|---|---|---|---|---|
| Example No. | Above 2 mm wt % | 2 to 0.9 mm wt % | 0.9 to 0.43 mm wt % | 0.43 to 0.3 mm wt % | Below 0.3 mm wt % |
| Example 1 | 40.5 | 46.2 | 10.4 | 1.3 | 1.5 |
| Example 2 | 49.8 | 42.9 | 5.6 | 0.8 | 1.0 |
| Example 4 | 56.6 | 34.2 | 6.7 | 1.2 | 1.2 |
| Example 5 | 55.3 | 38.5 | 4.7 | 0.8 | 0.6 |
| Comparative Example 1 | 10.0 | 37.3 | 42.1 | 4.5 | 6.6 |

The results in the Table 2 show that the catalysts according to the invention give polymers having much less polymer fines.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A catalyst component for olefin polymerization, comprising a reaction product of
   (1) a spherical magnesium halide adduct represented by the following formula (I):

$$MgX_2 \cdot mROH \cdot nEpH_2O \quad \text{(I)}$$

wherein X is chlorine or bromine; R is a $C_1$-$C_{12}$ alkyl, a $C_3$-$C_{10}$ cycloalkyl or a $C_6$-$C_{10}$ aryl; E is an o-alkoxybenzoate compound represented by formula (II):

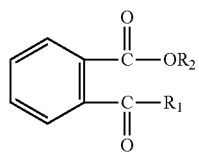

wherein $R_1$ and $R_2$ groups, which are the same or different, are independently a $C_1$-$C_{12}$ linear or branched alkyl, a $C_3$-$C_{10}$ cycloalkyl, or a $C_7$-$C_{10}$ aralkyl, the $R_1$ and $R_2$ groups are identical to or different from the R group;
   m is in a range of from 1.0 to 5.0;
   n is in a range of from 0.001 to 0.5; and
   p is in a range of from 0 to 0.8;
   (2) at least one titanium compound; and optionally
   (3) at least one electron donor compound.

2. The catalyst component of claim 1, wherein the at least one titanium compound has a general formula of $TiX_3$ or $Ti(OR^3)_{4-m}X_m$, in which $R^3$ is independently a $C_1$-$C_{14}$ aliphatic hydrocarbyl group, X is independently F, Cl, Br or I, and m is an integer of from 1 to 4.

3. The catalyst component of claim 2, wherein the at least one titanium compound is titanium tetrachloride.

4. The catalyst component of claim 1, wherein the at least one electron donor compound is chosen from esters, ethers, ketones, silanes, and amines.

5. The catalyst component of claim 4, wherein the at least one electron donor compound is chosen from esters of aliphatic and aromatic mono- and poly-basic carboxylic acids, esters of diols, and di-ethers.

6. The catalyst component of claim 5, wherein the at least one electron donor compound is chosen from benzoates, phthalates, malonates, succinates, glutarates, pivalates, adipates, sebacates, maleates, naphthalene dicarboxylates, trimellitates, benzene-1,2,3-tricarboxylates, pyromellitates, carbonates,
esters of diols represented by formula (III)

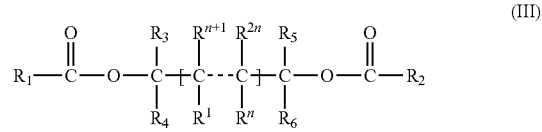

wherein $R_1$ to $R_6$ and $R^1$ to $R^{2n}$, which are the same or different, are independently hydrogen, halogen, optionally substituted linear or branched $C_1$-$C_{20}$ alkyl, $C_3$-$C_{20}$ cycloalkyl, $C_6$-$C_{20}$ mono-ring or multi-ring aryl, $C_7$-$C_{20}$ alkylaryl, $C_7$-$C_{20}$ arylalkyl, $C_2$-$C_{10}$ alkenyl, or $C_2$-$C_{10}$ ester group, with the proviso that $R_1$ and $R_2$ are not hydrogen, $R_3$ to $R_6$ and $R^1$ to $R^{2n}$ optionally comprise at least one heteroatom chosen from nitrogen, oxygen, sulfur, silicon, phosphorus and halogen, replacing at least one carbon or hydrogen or both contained therein, and at least two of $R_3$ to $R_6$ and $R^1$ to $R^{2n}$ groups are optionally linked to form a ring; and n is an integer ranging from 0 to 10, and
1,3-diether compounds represented by formula (VI):

wherein $R^I$, $R^{II}$, $R^{III}$, $R^V$ and $R^{VI}$, which are the same or different, are independently chosen from hydrogen, halogen, linear or branched $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl; $R^{VII}$ and $R^{VIII}$, which are the same or different, are independently chosen from linear or branched $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl; and at least two of $R^I$ to $R^{VI}$ groups are optionally linked to form a ring.

7. The catalyst component of claim 6, wherein the esters of diols are represented by formula (IV):

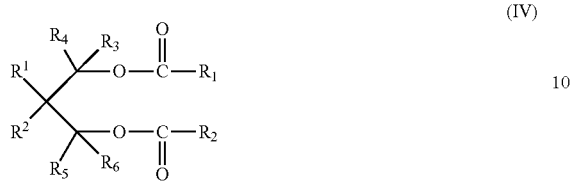

(IV)

wherein $R_1$ to $R_6$, $R^1$ and $R^2$, which are the same or different, are independently hydrogen, halogen, optionally substituted linear or branched $C_1$-$C_{20}$ alkyl, $C_3$-$C_{20}$ cycloalkyl, $C_6$-$C_{20}$ mono-ring or multi-ring aryl, $C_7$-$C_{20}$ alkylaryl, $C_7$-$C_{20}$ arylalkyl, $C_2$-$C_{10}$ alkenyl, or $C_2$-$C_{10}$ ester, with the proviso that $R_1$ and $R_2$ are not hydrogen, $R_3$ to $R_6$, $R^1$ and $R^2$ optionally comprise at least one heteroatom chosen from nitrogen, oxygen, sulfur, silicon, phosphorus and halogen, replacing at least one carbon or hydrogen or both contained therein, and at least two of $R_3$ to $R_6$, $R^1$ and $R^2$ are optionally linked to form a ring.

8. The catalyst component of claim 6, wherein the esters of diols are represented by formula (V):

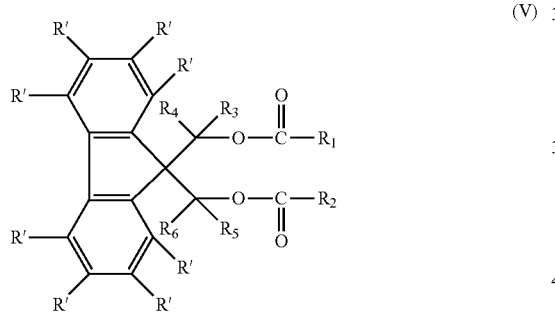

(V)

wherein $R_1$ to $R_6$, which are the same or different, are independently hydrogen, halogen, optionally substituted linear or branched $C_1$-$C_{20}$ alkyl, $C_3$-$C_{20}$ cycloalkyl, $C_6$-$C_{20}$ mono-ring or multi-ring aryl, $C_7$-$C_{20}$ alkylaryl, $C_7$-$C_{20}$ arylalkyl, $C_2$-$C_{10}$ alkenyl, or $C_2$-$C_{10}$ ester, with the proviso that $R_1$ and $R_2$ are not hydrogen, $R_3$ to $R_6$ optionally comprise at least one heteroatom chosen from nitrogen, oxygen, sulfur, silicon, phosphorus and halogen, replacing at least one carbon or hydrogen or both contained therein, and at least two of $R_3$ to $R_6$ are optionally linked to form a ring; and wherein R's are independently hydrogen, halogen, linear or branched $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl.

9. The catalyst component of claim 1, wherein the R group of the spherical magnesium halide adduct is a $C_1$-$C_4$ alkyl.

10. The catalyst component of claim 1, wherein the $R_1$ and $R_2$ groups of the spherical magnesium halide adduct are independently a $C_1$-$C_6$ linear or branched alkyl or a $C_3$-$C_5$ cycloalkyl.

11. The catalyst component of claim 10, wherein the $R_1$ and $R_2$ groups of the spherical magnesium halide adduct are independently methyl, ethyl, n-propyl, isopropyl, n-butyl or iso-butyl.

12. The catalyst component of claim 1, wherein in the spherical magnesium halide adduct, m ranges from 1.5 to 3.5, and n ranges from 0.005 to 0.2.

13. The catalyst component of claim 1, wherein the X of the spherical magnesium halide adduct is chlorine.

* * * * *

UNITED STATES PATENT AND TRADEMARK OFFICE
CERTIFICATE OF CORRECTION

PATENT NO. : 10,239,969 B2  
APPLICATION NO. : 15/292467  
DATED : March 26, 2019  
INVENTOR(S) : Xianzhi Xia et al.

Page 1 of 1

It is certified that error appears in the above-identified patent and that said Letters Patent is hereby corrected as shown below:

In the Claims

Claim 6, Column 16, Line 63, ""wherein $R^I$, $R^{II}$, $R^{III}$, $R^V$ and $R^{VI}$, which are the same or" should read --wherein $R^I$, $R^{II}$, $R^{III}$, $R^{IV}$, $R^V$ and $R^{VI}$, which are the same or--.

Signed and Sealed this  
Third Day of September, 2019

Andrei Iancu  
*Director of the United States Patent and Trademark Office*